(12) United States Patent
Ward et al.

(10) Patent No.: US 11,779,235 B2
(45) Date of Patent: Oct. 10, 2023

(54) MULTI-SENSOR INTRACRANIAL PRESSURE MONITOR FOR CEREBRAL HEMODYNAMIC MONITORING

(71) Applicant: THE REGENTS OF THE UNIVERSITY OF MICHIGAN, Ann Arbor, MI (US)

(72) Inventors: Kevin R. Ward, Superior Township, MI (US); Kenn Oldham, Ann Arbor, MI (US); Lu Wang, Ann Arbor, MI (US); Sardar Ansari, Richmond, VA (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 565 days.

(21) Appl. No.: 16/793,650

(22) Filed: Feb. 18, 2020

(65) Prior Publication Data
US 2020/0260975 A1 Aug. 20, 2020

Related U.S. Application Data

(60) Provisional application No. 62/806,414, filed on Feb. 15, 2019.

(51) Int. Cl.
*A61B 5/03* (2006.01)
*A61B 5/00* (2006.01)
*A61B 5/0215* (2006.01)

(52) U.S. Cl.
CPC .......... *A61B 5/031* (2013.01); *A61B 5/0075* (2013.01); *A61B 5/0084* (2013.01); *A61B 5/02158* (2013.01); *A61B 2562/0233* (2013.01); *A61B 2562/0247* (2013.01); *A61B 2562/0271* (2013.01)

(58) Field of Classification Search
CPC ............ A61B 5/02055; A61B 5/14553; A61B 5/0261; A61B 5/02007; A61B 5/742; A61B 5/0538; A61B 5/6852; A61B 5/02158; A61B 5/02154; A61B 5/0215; A61B 5/0084; A61B 5/0075; A61B 5/032;
(Continued)

(56) References Cited

U.S. PATENT DOCUMENTS 4,600,017 A * 7/1986 Schroeppel .............. A61B 5/03
607/122
9,993,170 B1 6/2018 Oliveira et al.
(Continued)

OTHER PUBLICATIONS

AETNA, Thermal perfusion probe for monitoring regional cerebral blood flow, www.aetna.com (2018).
(Continued)

*Primary Examiner* — Alex M Valvis
*Assistant Examiner* — Chanel J Jhin
(74) *Attorney, Agent, or Firm* — MARSHALL, GERSTEIN & BORUN LLP

(57) ABSTRACT

Devices and techniques for continuously monitoring pressure and simultaneously monitoring changes in blood flow, vascular resistance, and/or vascular behavior are provided. The techniques are employed in measuring intracranial pressure (ICP), while simultaneously measuring cerebral blood flow and/or cerebrovascular resistance or behavior. A sensor device includes an optical and piezoelectric sensing assembly integrated into a deployable ICP monitoring device.

18 Claims, 14 Drawing Sheets

(58) Field of Classification Search
CPC ... A61B 5/03; A61B 5/031; A61B 2562/0271; A61B 2562/0247; A61B 2562/0233
See application file for complete search history.

(56) References Cited

U.S. PATENT DOCUMENTS

| | | | | |
|---|---|---|---|---|
| 2006/0079773 | A1* | 4/2006 | Mourad | A61B 5/031 600/438 |
| 2007/0232874 | A1* | 10/2007 | Ince | A61B 5/72 600/320 |
| 2010/0121214 | A1* | 5/2010 | Giftakis | A61N 1/36082 600/595 |
| 2013/0035577 | A1 | 2/2013 | Wolf, II | |
| 2014/0180030 | A1* | 6/2014 | Dorando | A61B 5/0215 600/301 |
| 2015/0119724 | A1* | 4/2015 | Weber | A61B 5/02007 600/478 |
| 2015/0265171 | A1* | 9/2015 | Seaver | A61B 5/0002 600/561 |
| 2018/0010974 | A1* | 1/2018 | Bueche | A61B 5/145 |
| 2018/0271491 | A1* | 9/2018 | Flanagan | A61B 8/54 |

OTHER PUBLICATIONS

Ansari et al., A novel portable polyvinylidene fluoride based sensor for hemorrhage, Circulation, 132(3):A18257 (2015).

Ansari et al., Real-time detection of intradialytic hypotension using a novel polyvinylidene fluoride based sensor, IEEE Biomedical Health Informatics Conference (2016).

Chesnut et al., A trial of intracranical-pressure monitoring in traumatic brain injury, New England Journal of Medicine, 367:2471-2481 (2012).

Chesnut, Intracranial pressure monitoring: headstone or a new head start. The Best Trip trial in perspective, Intensive Care Medicine, 39(4):771-774 (2013).

Choi et al., Multi-photon vertical cross-sectional imaging with a dynamically-balanced thin-film PZT z-axis microactuator, Journal of Microelectromechanical Systems, 26(5):1018-2029 (2017).

Duan et al., MEMS-based multiphoton endomicroscope for repetitive imaging of mouse colon, Biomedical Optics Express, 6(8):3074-3083 (2015).

Duan et al., Visualizing epithelial expression of EGFR in vivo with a distal scanning side-viewing confocal endomicroscope, Scientific Reports, 6:37315 (2016).

Farahver et al., Increased mortality in patients with severe traumatic brain injury treated with intracranial pressure monitoring, Journal of Neurosurgery, 117(4):729-734 (2012).

Lazaridis et al., Patient-specific thresholds and doses of intracranial hypertension in severe traumatic brain injury, Acta Neurochirurgica Supplement, 122:117-120 (2016).

Phillips et al., Cerebral arterial oxygen saturation measurements using a fiber-optic pulse oximeter, Neurocritical Care, 13(2):275-285 (2010).

Qiu et al., Targeted vertical cross-sectional imaging with handheld near-infrared dual axes confocal fluorescence endomicroscope, Biomedical Optics Expres, 4(2):322-330 (2013).

Sethuraman, Cerebral blood flow monitoring, Journal of Neuroanaesthesiology and Critical Care, 2:204-214 (2015).

Tiba et al., Novel noninvasive method of cerebrovascular blood vol. assessment using brain bioimpedance, Journal of Neurotrauma, 34:1-8 (2017).

Wang et al., Estimation of peripheral artery radius using non-invasive sensor and Kalman filtering of local dynamics, 2017 American Controls Conference, Seattle, WA, (2017).

Wang et al., Identification of compensatory arterial dynamics in swine using a non-invasive sensor for local vascular resistance (under review), in Proceedings of the ASME Conference on Dynamic Systems and Control, Atlanta, GA (2018).

Wang et al., Non-invasive vascular resistance monitoring with a piezoelectric sensor and photoplethysmogram, Sensors and Actuators A: Physical, 263:198-208 (2017).

* cited by examiner

MULTI-SENSOR INTRACRANIAL PRESSURE MONITOR FOR CEREBRAL HEMODYNAMIC MONITORING

CROSS-REFERENCE TO RELATED APPLICATIONS

This application claims the benefit of U.S. Provisional Application Ser. No. 62/806,414, filed Feb. 15, 2019, the entirety of which is hereby incorporated herein by reference.

FIELD OF THE DISCLOSURE

The present disclosure relates to insertable pressure monitors and, more particularly, to multi-sensor intracranial pressure monitors.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Traumatic brain injuries (TBIs) can result from many different causes, such as, head trauma, aneurysms, brain tumors, infection, hypoxia, and stroke. The effects of TBI can vary greatly, patient to patient. In general, however, whatever the cause, medical staff (typically emergency room staff) look to treat TBIs as quickly and as effectively as possible. Of particular importance is that TBIs are often followed by secondary ischemic damage to the brain that results from decreased blood flow due to high intracranial pressure (ICP). Current methods of monitoring ICP and blood flow within the brain rely on intermittent imaging. But these imaging techniques lack the sensitivity and dynamic readouts that allow physicians to make appropriate and rapid treatment decisions when time is the most critical factor for improving prognosis. There is, as a result, a substantial unmet medical need for continuous monitoring of ICP and blood flow, and to do so using technologies that can be easily adapted and used in the emergency room clinical setting.

SUMMARY OF THE INVENTION

The present techniques include devices and techniques for continuously monitoring pressure and simultaneously monitoring changes in blood flow, vascular resistance, and/or vascular behavior. These techniques may be employed in measuring intracranial pressure (ICP), for example, while simultaneously measuring cerebral blood flow and/or cerebrovascular resistance or behavior. The continuous monitoring techniques herein can be used to provide precision cerebrovascular management of traumatic brain injuries (TBI) or similar conditions.

In exemplary embodiments, the present techniques are implemented through a sensor device designed having an optical and piezoelectric sensing assembly integrated into a deployable ICP monitoring device. The result is a multiple sensor pressure monitoring device capable of measuring and tracking vascular resistance and behavior while simultaneously monitoring pressure. In some examples, this multiple sensor pressure monitoring device includes a controller configured to estimate local arterial radius changes as a result of the arterial pressure information and correspondingly tracks blood flow and vascular reactivity. The addition of blood flow and vascular reactivity data, with pressure data, allows for more accurate, continuous tracking of the conditions of a test region, thereby allowing clinicians to better control treatment of an area of too high pressure. In some exemplary embodiments, the tracking of blood flow and vascular reactivity is performed on a heartbeat-by-heartbeat basis to allow for highly accurate measurement and quick responsiveness at critical moments of treatments.

In exemplary embodiments, a system is provided for monitoring pressure, such as intracranial pressure along with blood value, where the system is able to determine proportional fluctuations in arterial volume versus pressure during each heartbeat and correlate those proportional fluctuations with vascular resistance/behavior. In some embodiments, heartbeat-by-heartbeat waveforms from piezoelectric sensors measuring pressure and optical sensors measuring for blood volume are collected and compared to develop a time dependent vascular resistance. From the determination of vascular resistance and pressure, blood flow can then be determined thereby indicating to clinicians to continuous changes to an area under inspection. These determinations can therefore show, in real time, the effects of attempts to alleviate ICP and/or enhance cerebral blood flow and cerebral autoregulation.

In accordance with an example, an insertable catheter apparatus comprises: a pressure sensor at a distal end of the catheter and configured to measure first pressure data of a sample region within a subject; an optical sensor positioned proximally from the pressure sensor and configured to illuminate an optical sample region and to collect reflected illumination from the optical sample region, the reflected illumination corresponding to blood volume in the optical sample region; a piezoelectric pressure sensor positioned adjacent the optical sensor and covering a periphery of the insertable catheter, the piezoelectric pressure sensor configured to measure pressure data for the optical sample region; and a processing device configured to receive the reflected illumination data from the optical sensor, receive the pressure data from the piezoelectric pressure sensor, and analyze the pressure data and reflected illumination data, heartbeat-by-heartbeat, and determine (i) vascular resistance over the optical sample region, (ii) a blood flow over optical sample region, and (iii) pressure over the optical sample region.

In accordance with another example, an insertable catheter apparatus comprises: a pressure sensor at a distal end of the catheter and configured to measure first pressure data of a sample region within a subject; an optical sensor positioned proximally from the pressure sensor and configured to illuminate an optical sample region and to collect reflected illumination from the optical sample region and to determine a differential absorption spectroscopy or to collect scattered illumination from the optical sample region and determine a resonance Raman spectroscopy, the reflected illumination or scattered illumination corresponding to tissue oxygenation and/or mitochondrial function in the optical sample region; a piezoelectric pressure sensor positioned adjacent the optical sensor and covering a periphery of the insertable catheter, the piezoelectric pressure sensor configured to measure pressure data for the optical sample region; and a processing device configured to receive reflected illumination data or scattered illumination data from the optical sensor, receive the pressure data from the piezoelectric pressure sensor, and analyze the pressure data and reflected illumination data or scattered illumination data, heartbeat-by-heartbeat, and determine (i) tissue oxygenation and mitochondrial function over the optical sample region, (ii) a blood flow over optical sample region, and/or (iii) pressure over the optical sample region.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 2 also illustrates a process of using an intracranial pressure sensing catheter (b), as may be issued in the system of FIG. 1, for high-bandwidth measurement of beat-to-beat local pressure and blood volume fluctuation and for determining autoregulatory behaviors, vascular resistance, blood flow, and local trends in cerebral blood flow, in accordance with an example.

DETAILED DESCRIPTION

Figure 1:
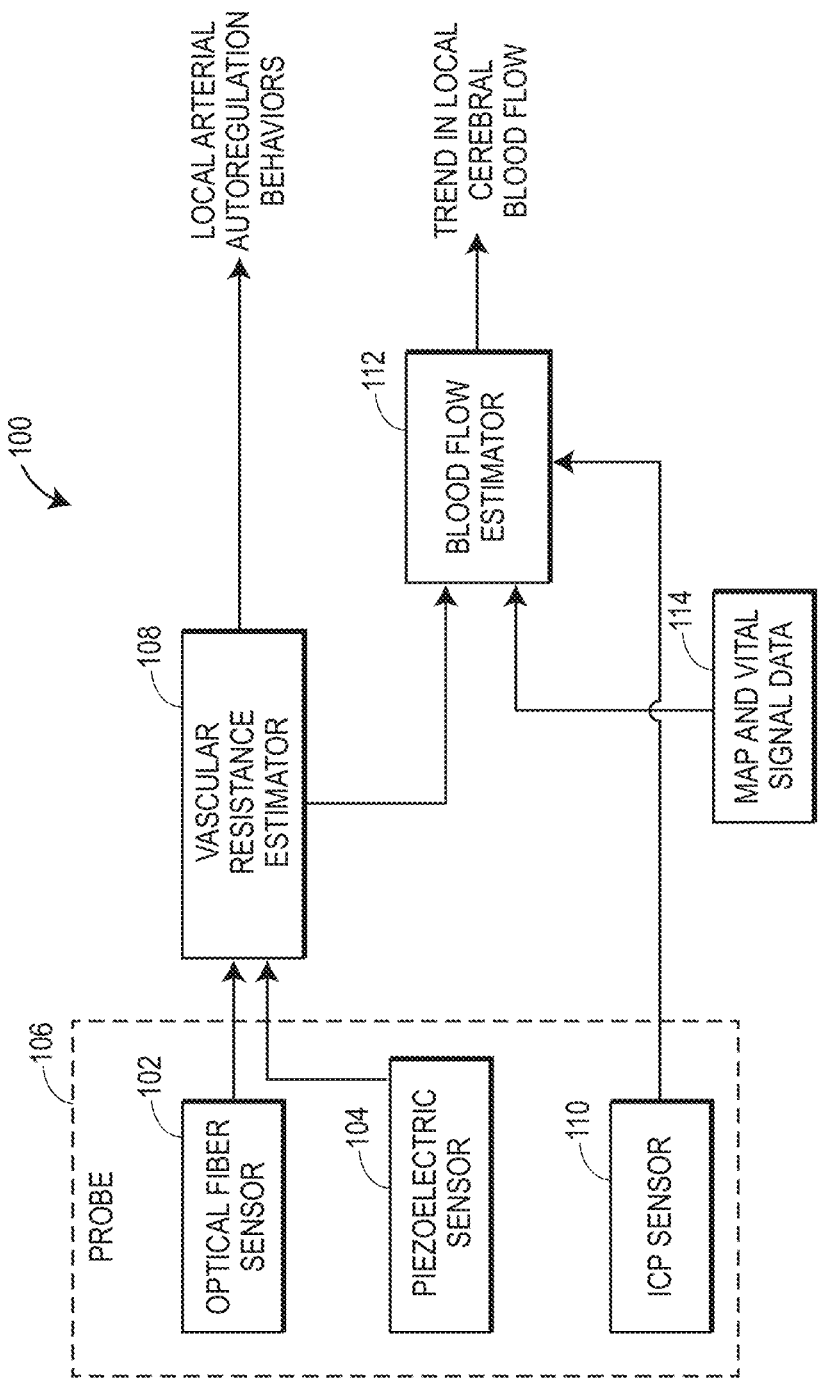
FIG. 1 is a schematic view of a multi-sensor pressure monitoring system, in accordance with an example.

The present techniques provide devices and methods for measuring and monitoring pressure and blood flow dependent measurements at an internal inspection region of a subject, such as within a blood vessel or within tissue, such as brain tissue. Example devices include insertable sensor devices, including for example insertable ICP devices, designed with additional sensors of different types. For example, in some exemplary devices, the present techniques are implemented in ICP devices with integrated optical sensors and piezoelectric sensors. The optical sensors may be configured to sensor blood related conditions in the inspection region and the piezoelectric sensors may be configured to sense arterial pressure or pressure over the inspection region, whether overlapping with that of the optical sensor or otherwise.

In exemplary embodiments, the present techniques include devices and techniques for continuously monitoring pressure and simultaneously monitoring changes in blood flow, vascular resistance, and/or vascular behavior. Employed for ICP measure, such devices simultaneously measure cerebral blood flow and/or cerebrovascular resistance or behavior, thereby providing for precision cerebrovascular management of traumatic brain injuries (TBI) or similar conditions where the brain is at risk for damage.

In exemplary embodiments, an ICP monitoring device is configured with miniature piezoelectric pressure and optical blood volume sensors that provide synchronized, high-bandwidth measurements of heartbeat-to-heartbeat local pressure and blood volume fluctuations. The multi-sensor combination of signals permits close tracking of relative constriction or dilation of nearby arteries, which can be used to track changes in blood flow given knowledge of arterial pressure.

In example implementations, the ICP monitoring device is integrated with an assembly of a piezoelectric thick-film and fiber optic enhancements and may be used in management of traumatic brain injury (TBI). In some examples, the ICP monitoring device is implemented as a ventriculostomy catheter or intraparenchymal monitor. In some examples, small diameter optical fibers are attached or embedded in a catheter lining, to measure local blood volume from light reflectivity measurements at one or more wavelengths. A piezoelectric polymer film may be attached around the circumference of the catheter tip to record real-time, heartbeat-to-heartbeat fluctuations in local pressure. The entire ICP monitoring device may be encapsulated in a conformal biocompatible polymer coating and communicatively coupled to a controller, such as an electrical and optical readout circuit.

In exemplary embodiments, the ICP monitoring device may thus be implemented as multiple-sensor ICP monitoring device is capable of measuring and tracking vascular resistance and behavior while simultaneously monitoring pressure and tissue oxygenation and metabolism. The controller may be configured to estimate local arterial radius changes from sensed arterial pressure information. The controller may be further configured to track blood flow and vascular reactivity. The addition of blood flow and vascular reactivity data, with pressure data, allows for continuous tracking of the conditions of the inspection region.

In some exemplary embodiments, the tracking of blood flow and vascular reactivity is performed on a heartbeat-by-heartbeat basis to allow for highly accurate measurement and quick responsiveness at critical moments of treatments.

In exemplary embodiments, a system is provided for monitoring pressure, such as intracranial pressure along with blood value, where the system is able to determine proportional fluctuations in arterial volume versus pressure during each heartbeat and correlate to those proportional fluctuations with vascular resistance/behavior.

In some embodiments, heartbeat-to-heartbeat waveforms from piezoelectric sensors measuring pressure and optical sensors measuring for blood volume are collected and compared to develop a time dependent vascular resistance. From the determination of vascular resistance and pressure, blood flow can then be determined thereby indicating to clinicians to continuous changes to an area under inspection. These determinations can therefore show, in real time, the effects of attempts to alleviate pressure, such as ICP.

In some embodiments, the waveform profiles developed herein are used to monitor changes in inferred blood flow distributions upstream from a monitor location.

In some embodiments, optical sensors can be placed for measuring brain tissue oxygenation and mitochondrial function, which may then be combined with piezoelectric sensor data and ICP sensor data, in accordance with the techniques herein.

In yet other examples, optical sensors may be used to measure tissue oxygenation and mitochondrial function using near infrared and/or near ultraviolet wavelengths and differential absorption spectroscopy or resonance Raman spectroscopy. In this way, the measured tissue oxygenation and mitochondrial function can be used to match brain metabolism with vascular function for identifying correlations between the two for diagnostic and treatment applications.

In yet further examples, additional sensors may be embedded in probe and catheter devices herein, including temperature sensors, actigraphy sensors, and impedance sensors.

In various examples, the present techniques herein provide numerous advantages over current diagnostic strategies for TBI directed at avoiding secondary ischemic injuries. The present techniques, for example, monitor cerebral blood flow along with ICP, for use in TBI management. Sensing and flow estimates now permit clinicians to determine whether regional blood flow is increasing, stable, or decreasing in response to interventions or as the body's response to trauma progresses.

FIG. 1 illustrates a multi-sensor pressure monitoring system 100 in accordance with an example of the present techniques. In the illustrated example the system includes an optical fiber sensor 102 and a piezoelectric sensor 104, both of which may be part of an insertable device such as a probe device 106. In some examples, the probe device 106 is a catheter device. In some examples, the probe device 106 is an intracranial pressure (ICP) probe device.

The optical sensor 102 may be an optical blood volume sensor. For example, the sensor 102 may be comprised of multiple optical fibers. At least one optical fiber delivers an illumination beam to a region of interest, where that optical output may be over any number of wavelength ranges, in particular those frequency ranges for measuring blood volume or arterial volume, such as over the near infrared, infrared, etc. For tissue oxygenation measurements, the near infrared ranges of 650-900 nm may be used for reflected light, while 405 nm maybe used for Raman scattered light detection. Particular useful wavelengths for reflected light are from 660 nm-680 nm. At least one other optical fiber collects reflected and/or scattered illumination from the region of interest and provides that collected illumination to a photodetector for collecting measurement data. The optical sensor 102 operates at a single illumination wavelength or it may operate over multiple illumination wavelengths, for example, to capture different data. In some examples, a probe may include a multimode fiber for collection multiple wavelengths, for example.

In some examples, the optical sensor 102, which includes the optical fibers, photodetector and photodetector controller (e.g., optical readout circuit), is configured for measuring blood flow and blood volume over a period of time, such as from heartbeat-to-heartbeat. In some examples, the optical sensor 102 may be further configured to additionally detect tissue and/or oxygenation levels. Indeed, in some such examples, the optical sensor 102 is configured to additionally perform as a pulse-oximetry sensor for measuring blood saturation levels and/or operating as a pulse plethysmography (PPG) sensor. More generally, the optical sensor 102 may be implemented any number of suitable biophotonic sensors, whether blood flow responsive, tissue responsive, tissue oxygenation or otherwise.

In an example operation, the optical sensor 102 may generate a continuous or pulsed illumination output beam via a light-emitting diode (LED) optically coupled to an illumination optical fiber for illumination a sample region with a subject. A reflected illumination light is captured by another optical fiber and transmitted to a photodetector that converts this illumination energy into an electrical current, which may be provided to a low noise electronic circuitry that, in some examples, includes a transimpedance (current-to-voltage) amplifier and filtering circuitry, forming part of a readout circuit (or controller). That controller may further include a high pass filter used to reduce the size of the dominant direct current (DC) component and to enable the pulsatile alternating current (AC) component to be amplified. The controller may further include a low-pass filter may be used to remove the unwanted higher frequency noise such as electric interference (i.e. 60 Hz noise).

The piezoelectric sensor 104 is configured to operate as a pressure sensor. For example, the piezoelectric sensor 104 may measure pressure changes generating an electrical signal and waveform (amplitude, width, time differences in peaks, delta responses to provocative movements such as breathing, volume infusion, etc.) that measures raw signal data that alters in response to blood pressure changes in a subject. In some examples, this data may be examined to determine circulating vascular volumes and vascular tone of a sample region.

In examples herein, the piezoelectric sensor 104 may be formed as a multilayer structure disposed around a circumference of the probe 106, where, for example, the sensor includes a first compliant polymer layer and a second compliant polymer layer both surrounding an electrode layer therebetween. The polymer layers may be pressure responsive surfaces to measure raw data correlative to changes in blood pressure or tissue pressure at a region of interest. The electrode layer may include one or more piezoelectric sensor electrodes. In some examples, those electrodes may be spaced apart by sufficiently small distances to facilitate highly sensitive raw data measurements under a force applied to the sensing layer resulting in a measurable change in a sensed voltage indicating pressure at the sample region.

In some examples, the piezoelectric sensor 104 is triggered manually, or in other examples a controller triggers the sensor automatically, e.g., in response to changes in pressure sensed by the probe 106 positioned within a subject. The same applies to a multi-sensor pressure monitoring system 100 the optical fiber sensor 102. Sensors 102 and 104 may be triggered, in some examples, by a user accessing software on a controller device, for example, through a touchscreen or other input device. In some examples, the sensors 102 and 104 may continuously collect raw signal data continually while positioned within a subject.

Figure 2:
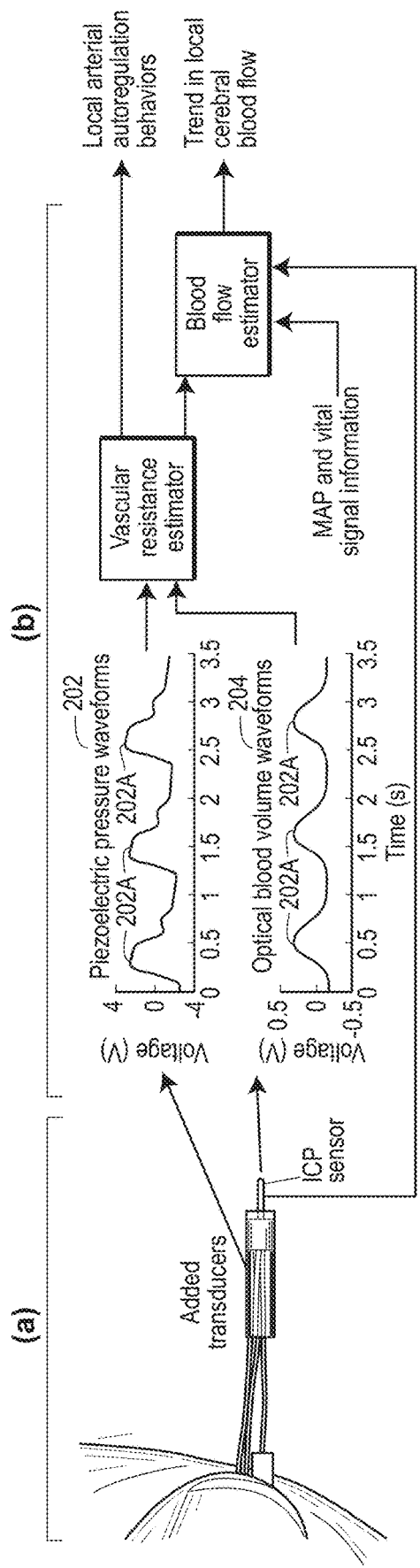
FIG. 2 illustrates an example multi-sensor, intracranial pressure sensing catheter (a).

In the illustrated example, the sensors 102 and 104 provide piezoelectric pressure waveform and optical blood volume waveforms, respectively, to a vascular resistance estimator 108. The waveforms may be high-bandwidth measurements of heartbeat-to-heartbeat local pressure and blood volume fluctuation over a sample region within a subject, such as a region within the brain of subject experience traumatic brain injury (TBI). FIG. 2 illustrates an example of the input waveforms 202 and 204, respectively.

The vascular resistance estimator 108 is configured to compare the two received signals and determine local arterial autoregulation behaviors. In some examples, the estimator 108 is configured to determine vascular resistance, radius, and/or stiffness, etc. by analyzing data from sensors 102 and 104 using developed vascular properties models. Example the systemic vascular resistance (SVR) models include an elliptical model that compares sensor data from both sensors 102 and 104 and determines an elliptical fit over a sample time frame, a technique also termed a hysteresis technique of vascular resistance/stiffness determination. In other examples, fluid dynamics between the positions the two sensors 102 and 104 may be taken into consideration, as well as additional dynamic states in what's termed a state-space model. The state-space model may include the effects of changing stiffness and/or radius in part of the state model. In other examples, the systemic vascular resistance (SVR) determination process may include automated radius tracking using an extended Kalman filter (EKF). The extended Kalman filter is a technique for tracking states and/or parameters of dynamic systems. In an example herein, sensor data from both the sensor 102 and the sensor 104 is provided to a state-space model that is used with extended Kalman filter to reduce signal error more quickly. Example implementations of these models for determining vascular resistance using information from two different sensors, specifically a piezoelectric sensor and an optical sensor may be found at U.S. application Ser. No. 16/344,671, filed Apr. 24, 2019, entitled, Estimation Of Peripheral Vascular Resistance Using A Miniature Piezoelectric Sensor, which is hereby incorporated herein, in its entirety.

While the estimator 108 is described as a vascular resistance estimator, in other examples, the estimator 108 may determine any number of vascular properties, such as vascular resistance, vascular stiffness, vascular radius, and/or applied power. In yet some examples, the vascular resistance estimator may estimate intervening tissue mechanical properties, optical absorbance, and viscoelasticity.

The multi-sensor pressure monitoring system 100 further includes another sensor 110, which may be an ICP sensor and may be formed as part of the probe device 106 along with the optical fiber sensor 102 and the piezoelectric sensor 104. In an ICP configuration, the sensor 110 may be an electrical conductor-based sensor or a polyurethane membrane-based sensor, examples of which include single pressure and multiple pressure catheters available from Millar Inc. or Houston, Tex.

The pressure sensed by the sensor 110 is output, along with the vascular resistance estimation from the estimator 108, and other vital sign data and mean arterial pressure (MAP) data 114 to a blood flow estimator 112. The MAP data may be, providing the average pressure in a subjects arteries during a heartbeat, may be determined from an external sensor, such as an invasive sensor or the MAP data may be calculated using the systolic blood pressure and diastolic blood pressure collected through non-invasive means. That is the, the MAP data may come from another location, such as a catheter in an artery, while the ICP data is coming from the intracranial catheter location to reflect pressure in the brain (either intraparenchymal or intraventricular). The blood flow estimator 112 is configured to determine local blood flow and trends in local blood flow from this data.

FIGS. 2-5 illustrate example implementations of the vascular resistance estimator 108 and the blood flow estimate 112. FIG. 2 illustrates example waveforms from the piezoelectric sensor 104 and the optical fiber sensor 102, respectively, as the waveforms would be provided to the vascular resistance estimator 108. Each waveform is characterized by periodic peaks 202A and 204A occurring each heartbeat, where there is a varying phase delay between the peaks of each waveform.

The estimator 108 compares these waveforms heartbeat-to-heartbeat and generates an estimated systemic vascular resistance (SVR). For example, the sensor 102 senses a change in volume in a sample region, such as changes in arterial volume, which the sensor 102 detects by illuminating sample region and measuring the amount of light reflected from that sample region. The voltage output of the sensor 102 is proportional to the change of the sample region volume. However, due to the transimpedance amplification and need for high-pass filtering to obtain the time-varying component of the light signal, conventionally-speaking optical sensors may not provide long term tracking of mean absolute arterial volume, but rather respond to short term fluctuations in arterial volume during cardiac cycles. In effect, changes in volume can be convoluted with amplifier and filter dynamics, which include a differentiation, then integrated to return the relative volume fluctuations. As a result, the estimator 108 may apply a model for determining vascular resistance based on measurements from the sensor 102. For the model, we applied a model of photoplethysmograph (PPG) voltage output, $u_{PPG}$, as:

$$u_{PPG}=K_{PPG}\int h_{PPG}*V_i dt = K_{PPG}\int h_{PPG}*\pi r_i^2 L_{PPG} dt \quad (1)$$

where $K_{PPG}$ is the gain of the sensor 102, $h_{PPG}$ is the linear dynamic filter response, and $V_i$ is volume of oxygenated blood between the LED light source of the sensor 102 and the photodetector. The volume, $V_i$, can alternatively be related to the inner radius of the artery $r_i$ and length of artery illuminated by the PPG, $L_{PPG}$. The length of the artery under the sensor 102 is assumed constant. It is noted that while a linear relationship between optical sensor output voltage and vascular volume is applied in these examples, in other examples, a non-linear and/or time-varying relationship between optical sensor output voltage and length may be applied. Further, ICP can be determined directly from the volume fluctuations in the illuminated area, given that the volume change will be larger for larger vessel radii and lesser when smaller vessel radii.

In the electrical domain, the piezoelectric sensor 104 (also termed "PVDF sensor 104") can be modeled as a charge source in parallel with the sensor's capacitance. The estimator 108 may include sensing circuitry that includes a high impedance charge mode amplifier to convert electrical charge to voltage. To compensate for low current from the PVDF sensor 104, i.e., current measured around 1-5 nA, that sensing circuitry may further included a stage amplifier, followed by a low pass filter stage that helps minimize electrical interference and high frequency noise. Charge, q, generated on the PVDF sensor 104 is given by:

$$q = d_{31} E A \varepsilon_1 \qquad (2)$$

where $d_{31}$ is the piezoelectric strain coefficient from tangential strain to charge displacement in the electrode direction, is the elastic modulus of the PVDF of the sensor 104, A is the surface area of the PVDF of the sensor 104, and $\varepsilon_1$ is the tangential strain in the PVDF layer of the sensor 104. In the model of Expression (2), compressive piezoelectric response (i.e., piezoelectric strain coefficient in the axial or electrode direction, $d_{33}$) and coupling effects are neglected as small compared to the dominant response from hoop stress around the ring formed by the sensor. In other examples, e.g., of other piezoelectric materials, the charge may be generated to a greater degree by other piezoelectric axes (i.e., $d_{33}$ piezo coefficient). The combined electrical model of the PVDF sensor 104 and sensing circuitry of the estimator 108, with resulting transfer function, $H_{PVDF}(s)$:

$$H_{PVDF}(s) = \frac{s}{RCs+1} \cdot \frac{K_{amp} \omega_{LPF}}{s + \omega_{LPF}} = \frac{18s}{(s+6)(s+178)} \qquad (3)$$

where R is the input resistance to the sensing circuit 2000 (e.g., 10 MOhm), C is the PVDF sensor capacitance, $K_{amp}$ is the net amplifying circuit gain, and $\omega_{LPF}$ is a low pass filtering frequency set by the second stage of the sensing circuit. Even with a relatively large amplifier resistance used to maintain a high input impedance for the small capacitance and charge generation of the PVDF material, the RC time constant of the sensor 104 is small, and its associated corner frequency in Expression (3) is much higher than frequencies of interest in the pressure waveform. Thus, the raw voltage output of the sensing circuitry of the estimator 108 is approximately proportional to the derivative of the charge generated or pressure.

In some examples, the present techniques account for variation in pressure experienced by the PVDF sensor 104, for example, by integrating the convolution of the time-varying charge with the amplifier dynamic response from Expression (3), $h_{pvdf}$, to produce a the final PVDF sensor output used for analysis, $u_{PVDF}$:

$$u_{PVDF} = \int h_{PVDF}(t) * q(t) dt \qquad (4)$$

The integration is used because the small charge amplitude and relative impedance of the sensor result in a high-pass filter cut-off frequency much higher than the frequency of cardiac cycles; integration returns this to an output approximately proportional to blood pressure, but mediated by intervening tissue, as discussed below. In other examples, a time-varying and/or nonlinear gain relationship may be used instead, through the use of other circuit models or if through the use of other piezoelectric materials. When we plotted examples of these $u_{PPG}$ and $u_{PVDF}$ determinations, we see that non-invasive tracking of SVR based on differential pressure versus differential volume trajectories shows close agreement with gold standard measurements.

Figure 3:
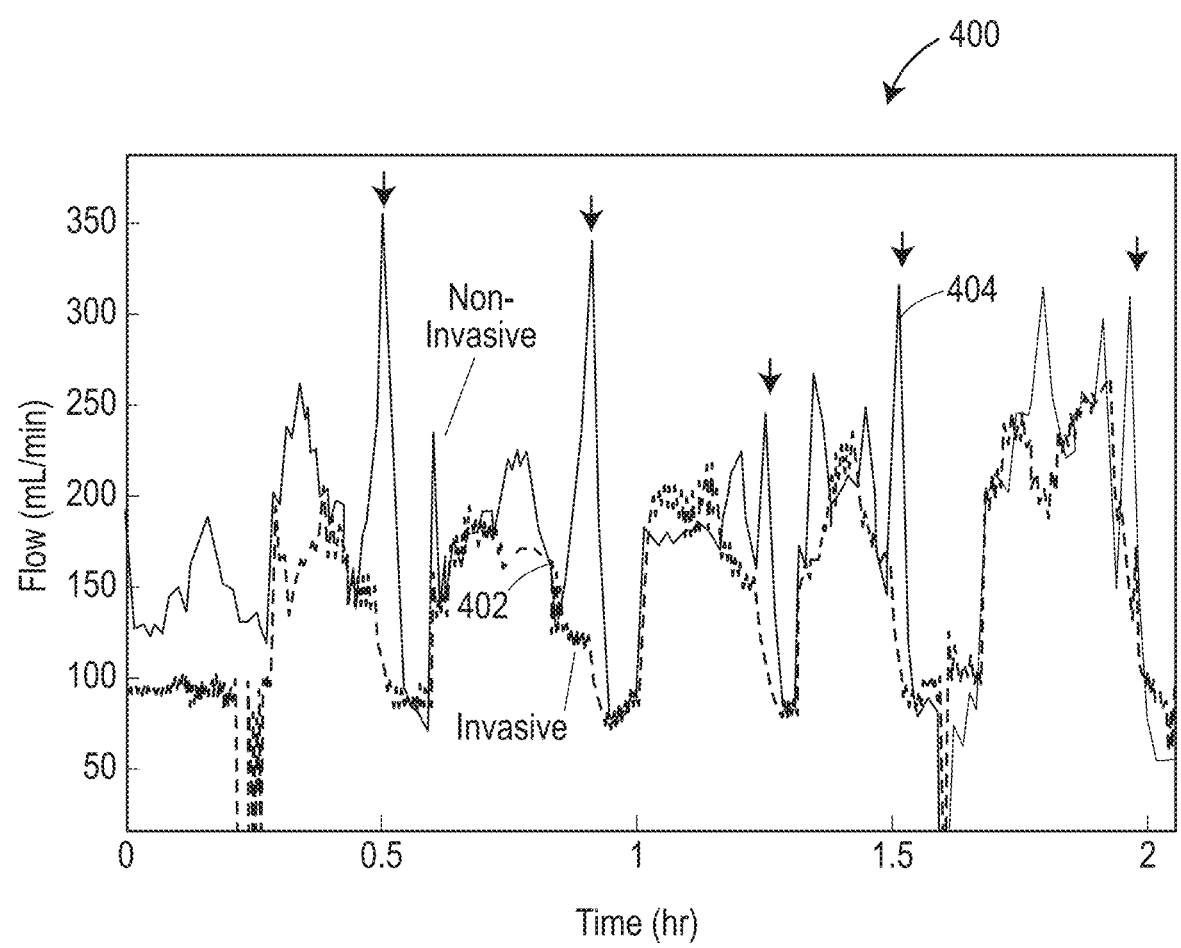
FIG. 3 illustrates blood flow shows agreement between invasive measurement in the sub-clavicular artery and estimates based on vascular resistance models, with deviation primarily occurring when infusions start and, especially, stop (arrows), attributed to local behavior mismatch with larger regional effects. Estimated flow is in arbitrary units and scaled to the invasive measurement for comparison.

With the systemic vascular resistance determined by the estimator 108, that signal is provided to the blood flow estimator 112, along with local pressure data from the ICP sensor 110 (and other ICP and MAP data 114), for calculating a blood flow, as shown in FIG. 3. Graph 400 shows a sample calculation of blood flow using the system 100 as shown in plot 402 compared against an external reference blood flow determined plot 404.

Figure 4:
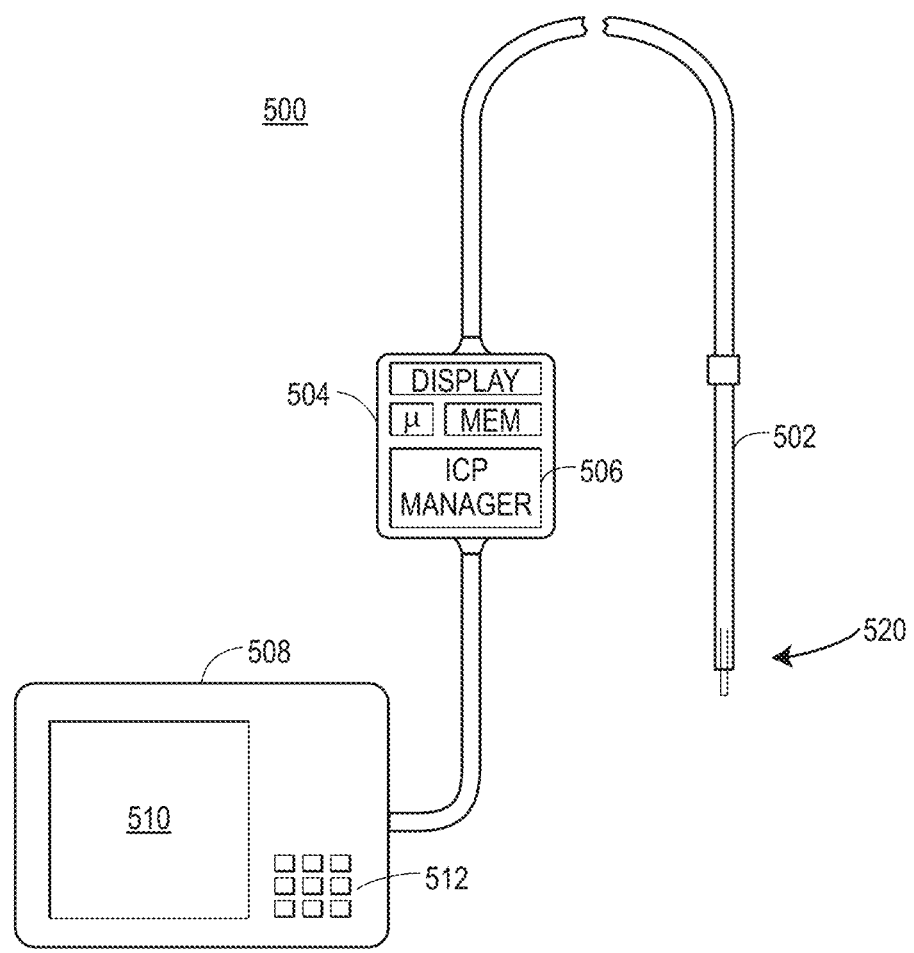
FIG. 4 is a schematic illustration of an example pressuring sensing system having a probe device with multiple sensors for pressure monitoring, and in particular, for intracranial pressure monitoring for cerebral hemodynamic monitoring, in accordance with an example.
Figure 5:
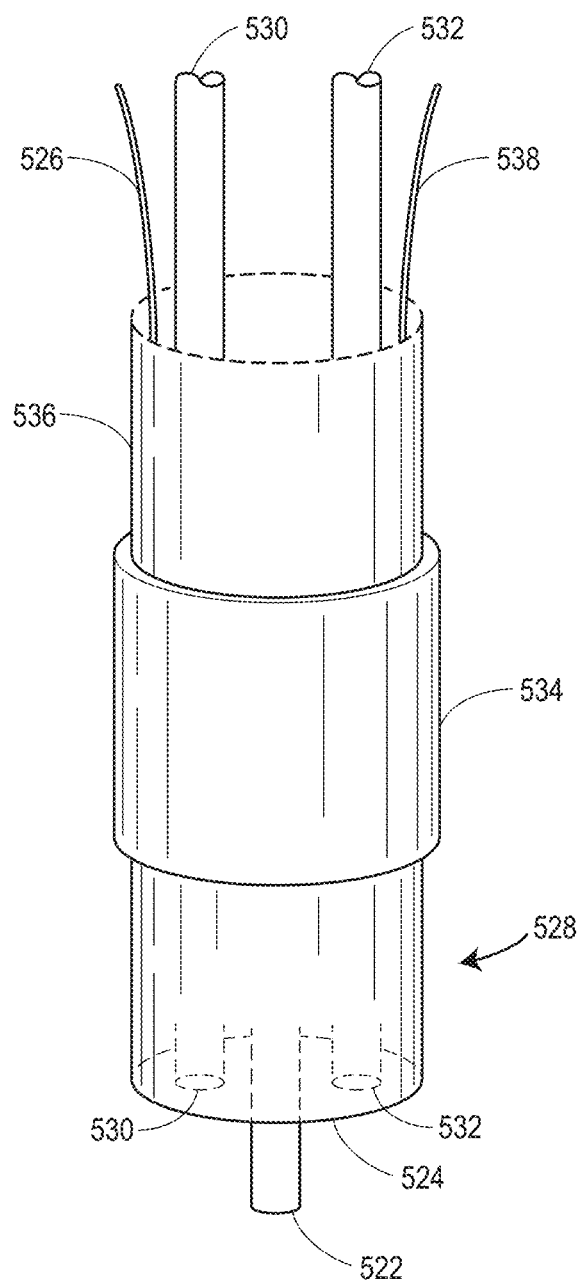
FIG. 5 is an illustration of a sensing end of the probe device of FIG. 4 having an end pressure sensor, an optical blood volume sensor, and a piezoelectric pressure sensor, in accordance with an example.

FIG. 4 illustrates an example pressuring sensing system 500 having a probe device 502 having multiple sensors for pressure monitoring, and in particular, for some examples, for intracranial pressure monitoring for cerebral hemodynamic monitoring, in accordance with examples herein. For example, in some implementations the probe device 500 may be an insertable catheter device, such as an intraparenchymal and/or intraventricular catheter used for ICP monitoring in subjects. Other examples include an epidural pressure catheter.

The pressure sensing system 500 includes a controller 504 communicatively coupled to the probe device 502. The controller 504 may include one or more displays, processors, and memories storing instructions to execute processes described herein. In the illustrated example, the controller 504 includes a pressure manager 506, which may be an ICP manager, configured to execute pressure, volume, resistance, and other computation operations described herein. For example, the ICP manager 506 may be configured to perform the functions of the vascular resistance estimator and blood volume estimate of FIG. 1. The controller 504 is also communicatively coupled to a care provider interface station 508, which has a display 510 and haptic input/keypad 512. The controller 504 controls operation of the probe device 502 including controlling illumination of a sample region, when the probe device 502 is deployed at a sample region. The probe device 502 further controls collection of pressure data over the sample region. Toward that end, in some examples, the controller 504 includes an illumination source, such as an LED near infrared light source coupled to the probe device 502, and a photodetector assembly to detect illumination captured by the probe device 502. The controller 504 may further include electrode connections for coupling to electrodes of the probe device 502, thereby establishing an electrical connecting to one or more sensors of the probe device 502.

In the illustrated example (see, e.g., FIG. 5), the probe device 502 has a distal end 520 formed with a primary sensor, in this example, an ICP sensor 522. The probe device 502 may be generally cylindrical in shape with a circular cross-section, and the ICP sensor 522 may be disposed along a central axis of the probe device 502. The ICP sensor 522 is positioned at an outer cap surface 524 of the probe device 502. In some examples, the ICP sensor 522 may be flush with that cap surface 524. In some examples, the ICP sensor 522 may extend distally from the cap surface 524. An electrode 526 is coupled to receive electrical pressure signals from the ICP sensor 522 and communicate those to the controller 504, e.g., to a readout circuit within the controller 504.

Figure 6A:
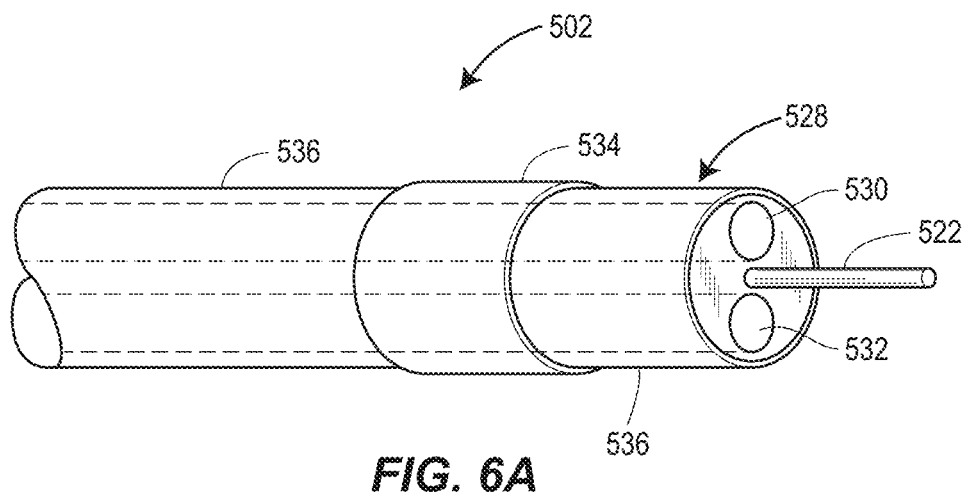
FIGS. 6A and 6B are perspective and end views of the sensing end of the probe device of FIG. 6, in accordance with an example.
Figure 6B:
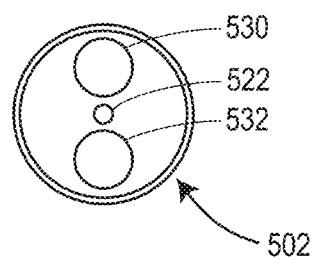

Extending upward from the ICP sensor 522 is an optical sensor 528 formed of two optical fibers 530 and 532, one for providing an illumination output beam to the sample region and the other for collecting a reflected (or in some examples scattered) illumination beam from the sample region. As shown, in FIGS. 6A and 6B, the optical fibers 530 and 532 may be located on opposite sides of the ICP sensor 522 and extend axially toward a proximal end of the probe device 502. Whereas the ICP sensor 522 is positioned to examine pressure in the portion of the sample region at or extending outwardly from the end of the probe device 502, in the illustrated configuration, the optical sensor 528 senses blood volume over a portion of the sample region adjacent thereto but extending upwardly from the end of the probe device 502. The sensing region of the optical sensor 528 may be defined by having transparent or translucent windows formed in a sheathing (not shown) of the probe device 502, or in other examples, the sheathing may be transparent or translucent at least over the desired sensing region.

The probe device 502 further includes a piezoelectric sensor 534, which is positioned around an outer surface 536 of the probe device 502 (flush with a sheathing if a sheathing is used), and positioned to coincide with the sensing region of the optical sensor 528, such that both sensors 528 and 534 sense blood volume and pressure, respectively, over the same region and different from the sensing region of the ICP sensor 522. For example, the piezoelectric sensor 534 may be adjacent the optical sensor 528, along a longitudinal direction. The piezoelectric sensor 534 may be partially or fully overlap the optical sensor 528, along the longitudinal direction. The piezoelectric sensor 534 is coupled to the controller 504 through a second electrode 538.

In an example, the piezoelectric sensor 534 is formed of one or more thin layers of polyvinylidene difluoride (PVDF) and encapsulating polymers around a piezoelectric layer. The piezoelectric sensor 534 may be deployed around an insertable catheter and may be formed with a elastomeric substrate onto which is formed a piezoelectric sensor region. That elastomeric substrate may be biocompatible, have similar elastic modulus to the PVDF film, and preferably have thicknesses on the order of 10-100 microns. The piezoelectric sensor region may extend a sufficient length of the substrate to allow for sensing over circumferential range of the insertable catheter. One or more electrodes may extend from the piezoelectric sensor region for driving the piezoelectric sensor and for generating sensed pressure signals.

The piezoelectric sensor 534 may be further formed of first and second encapsulating layers, sandwiching a piezoelectric layer and electrode layers that form the embedded pressure sensor region. In some examples, the piezoelectric sensor 534 may further include other embedded sensors, such as temperature sensors, motion sensors, actigraphy sensors, galvanic skin response sensors, impedance sensors, or any combination thereof.

Figure 8:
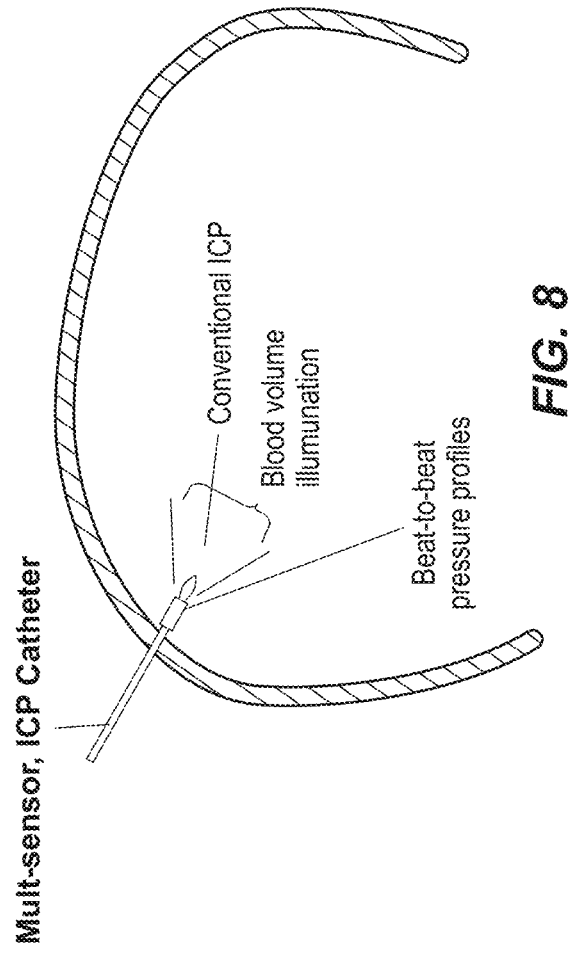
FIG. 8 illustrates a schematic arrangement of the multi-sensor, intracranial pressure sensing catheter deployed in the cranium for measurement, in accordance with an example.
Figure 7:
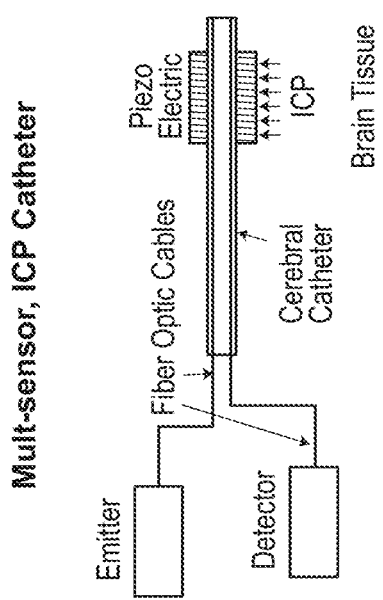
FIG. 7 illustrates a schematic of an example multi-sensor, intracranial pressure sensing catheter, in accordance with an example.

FIG. 7 illustrates a schematic of an example multi-sensor, intracranial pressure sensing catheter. FIG. 8 illustrates a schematic arrangement of the multi-sensor, intracranial pressure sensing catheter deployed in the cranium for measurement.

Figure 9:
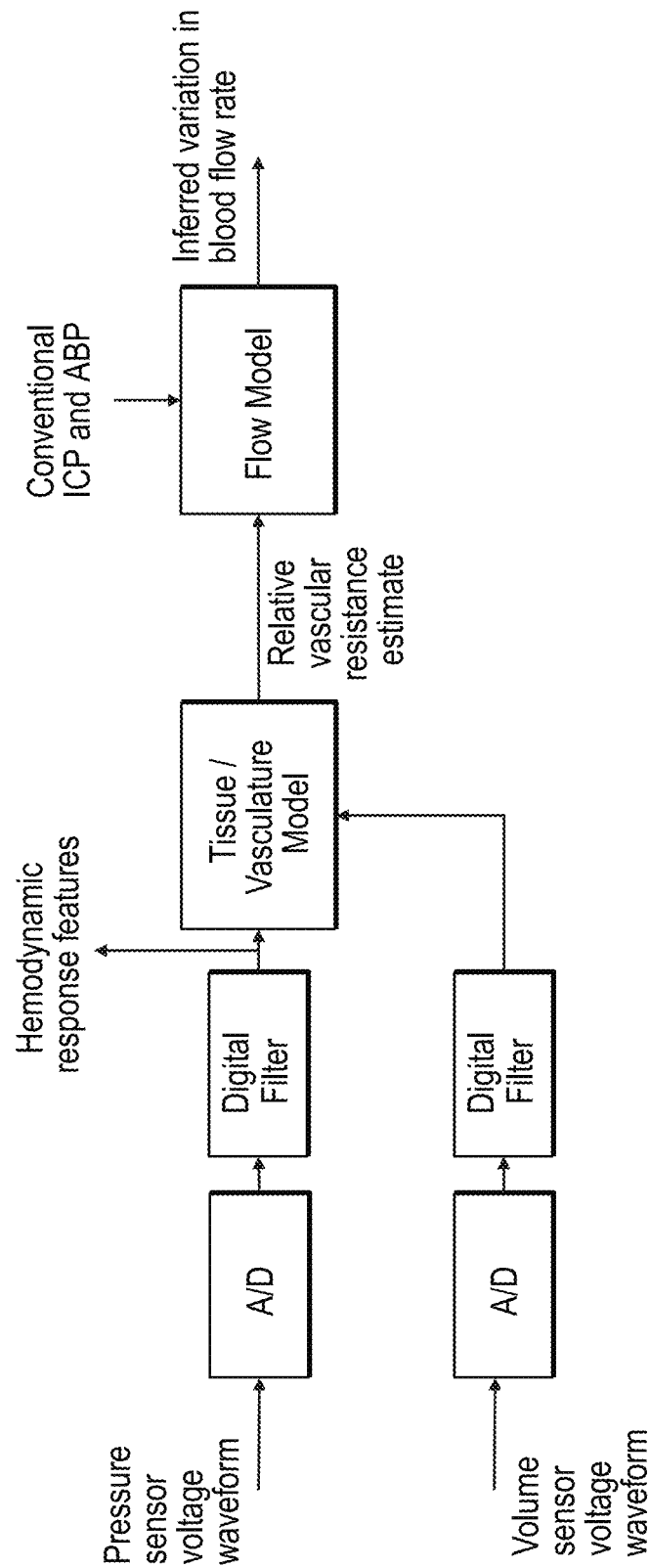
FIG. 9 illustrates another example processing schematic showing the generation of an inferred variation in blood flow rate, as determined from input pressure sensor voltage waveforms and input volume sensor voltage waveforms from the multi-sensor, ICP catheter, in accordance with an example.
Figure 10:
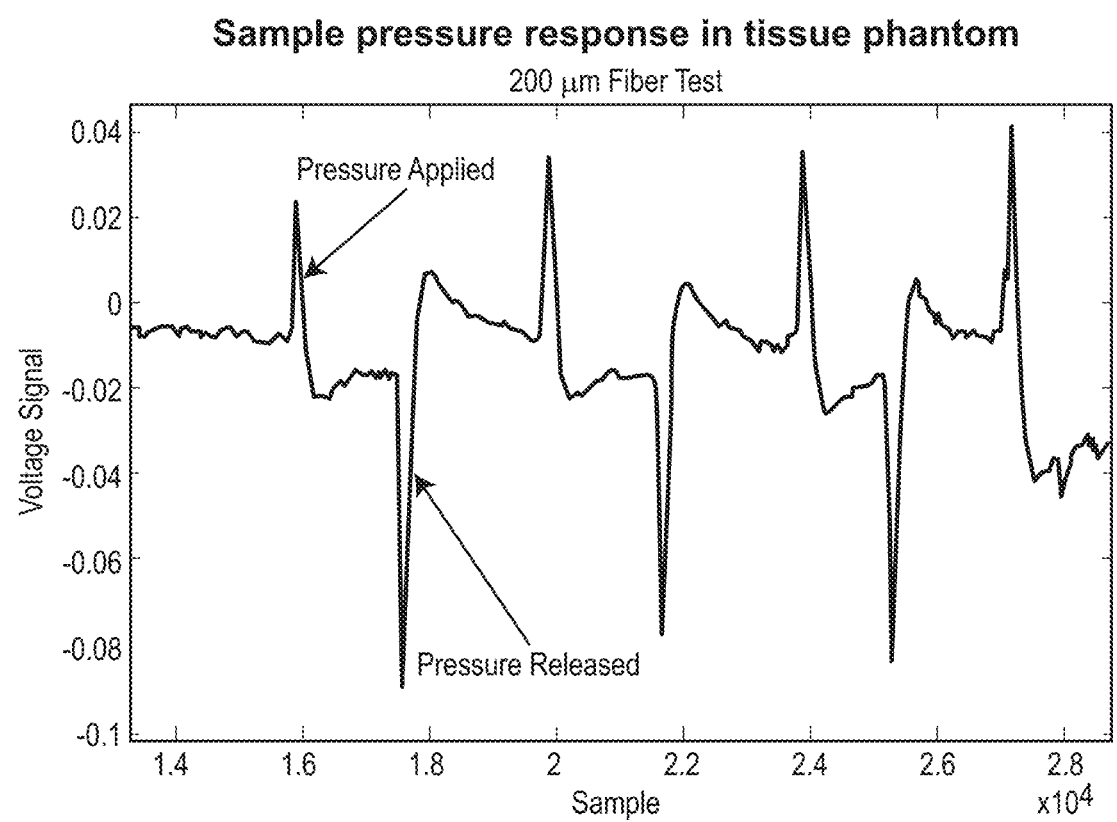
FIG. 10 illustrates the sample pressure response data in tissue phantom from an example application of the schematic in FIG. 9, in accordance with an example.

FIG. 9 illustrates another example processing schematic 800 showing the generation of an inferred variation in blood flow rate, as determined from input pressure sensor voltage waveforms and input volume sensor voltage waveforms from the multi-sensor, ICP catheter. In the illustrated example, the pressure sensor waveform and voltage sensor waveforms pass through analog-to-digital converters (802A, 804A) and digital filters (802B, 804B), respectively. A tissue/vasculature model 806 is used, similar to the vascular resistance estimator, to generate relative vascular resistance estimate data that is provided to a flow model 808 that also receives, in this example, conventional ICP data and arterial blood pressure (ABP) data, from which variations in blood flow rate are determined implementing the techniques above. FIG. 10 illustrates the sample pressure response data in tissue phantom from an example application of the schematic in FIG. 10.

Figure 11:
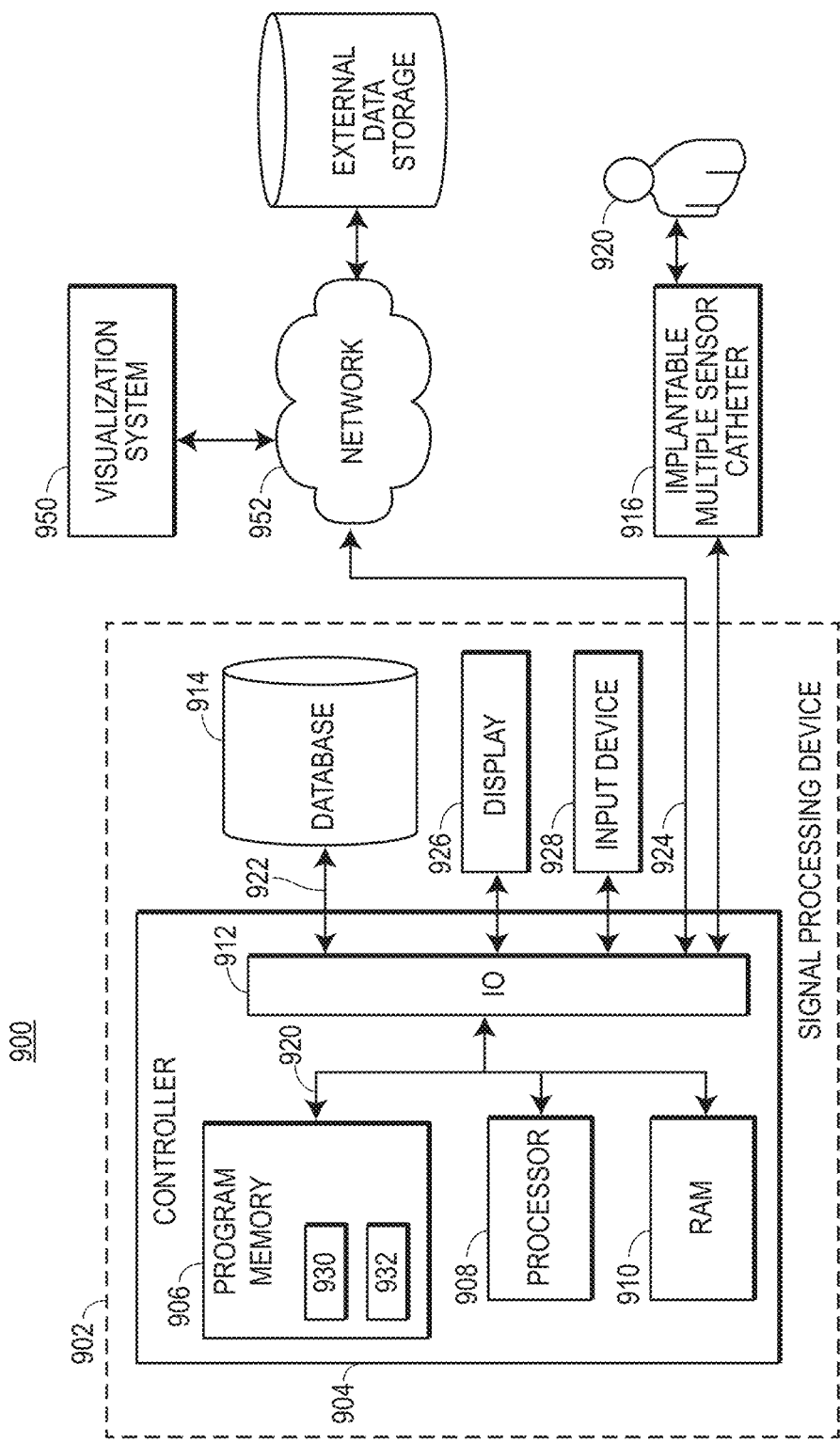
FIG. 11 is a schematic illustration of a piezoelectric cardiovascular monitoring system, in accordance with an example.

FIG. 11 is an example block diagram 900 illustrating the various components used in implementing an example embodiment of a piezoelectric cardiovascular monitoring system discussed herein. A signal-processing device 902 (or "signal processor") may be configured to examine a patient 920 via one or more wearable insertable multiple sensor catheters 916 (or a "insertable probe devices") in accordance with executing the functions of the disclosed embodiments. The signal-processing device 902 may have a controller 904 operatively connected to the database 914 via a link 922 connected to an input/output (I/O) circuit 912. It should be noted that, while not shown, additional databases may be linked to the controller 904 in a known manner. The controller 904 includes a program memory 906, one or more processors 908 (may be called microcontrollers or a microprocessors), a random-access memory (RAM) 910, and the input/output (I/O) circuit 912, all of which are interconnected via an address/data bus 920. It should be appreciated that although only one processor 908 is shown, the controller 904 may include multiple microprocessors 908. Similarly, the memory of the controller 904 may include multiple RAMs 910 and multiple program memories 906. Although the I/O circuit 912 is shown as a single block, it should be appreciated that the I/O circuit 912 may include a number of different types of I/O circuits. The RAM(s) 910 and the program memories 906 may be implemented as semiconductor memories, magnetically readable memories, and/or optically readable memories, for example. A link 924, which may include one or more wired and/or wireless (Bluetooth, WLAN, etc.) connections, may operatively connect the controller 904 to the insertable catheter 916 through the I/O circuit 912. The insertable catheter 916 may be operatively connected to the patient 920 by being inserted into the patient, for example inserted into the brain of the patient for measuring for ICP.

The program memory 906 and/or the RAM 910 may store various applications (i.e., machine readable instructions) for execution by the processor 908. For example, an operating system 930 may generally control the operation of the signal-processing device 902 and provide a user interface to the signal-processing device 902 to implement the processes described herein. The program memory 906 and/or the RAM 910 may also store a variety of subroutines 932 for accessing specific functions of the signal-processing device 902. By way of example, and without limitation, the subroutines 932 may include, among other things: a subroutine for taking optical and piezoelectric measurements with the insertable catheter 916, a subroutine for filtering measurement (or data) from the insertable catheter 916, a subroutine for performing signal decomposition on raw signal data from the insertable catheter 916, and a subroutine for extracting one or more features of a sensing region from the raw signal data from the insertable catheter 916.

The subroutines 932 may also include other subroutines, for example, implementing software keyboard functionality, interfacing with other hardware in the signal-processing device 902, etc. The program memory 906 and/or the RAM 910 may further store data related to the configuration and/or operation of the signal-processing device 902, and/or related to the operation of the one or more subroutines 932. For example, the data may be data gathered by the wearable sensor 916, data determined and/or calculated by the processor 908, etc. In addition to the controller 904, the signal-processing device 902 may include other hardware resources. The signal-processing device 902 may also include various types of input/output hardware such as a visual display 926 and input device(s) 928 (e.g., keypad, keyboard, etc.). In an embodiment, the display 926 is touch-sensitive, and may cooperate with a software keyboard routine as one of the software routines 932 to accept user input. It may be advantageous for the signal-processing device 902 to communicate with a broader medical treatment network (not shown) through any of a number of known networking devices and techniques (e.g., through a commuter network such as an hospital or clinic intranet, the Internet, etc.). For example, the testing apparatus may be connected to a medical records database (or other network-accessible external data storage connected through a wireless network 952), hospital management processing system, health care professional terminals (e.g., doctor stations, nurse stations), patient monitoring systems, automated drug delivery systems such as smart pumps, smart infusion systems, automated drug delivery systems, etc. or any type of network-accessible visualization system 950. Accordingly, the disclosed embodiments may be used as part of an automated closed loop system or as part of a decision assist system.

Although depicted as separate entities or components in FIG. 1, it is understood that any or the entire signal processing functionality and/or components of the signal-processing device 902 may be combined with a probe assembly, such as the probe sensing system 500 of FIG. 4.

As described herein, the insertable catheter 916 may include both a main pressure sensor, as well as an additional piezoelectric pressure sensor for measuring raw signal pressure data and optical sensor for measuring derived blood volume data. Examples of the insertable catheter 916 are provided in reference to FIGS. 5-8.

Experiment

We tested the insertable catheter techniques herein, in an example test of cranial blood flow in swine. A probe assembly was inserted into a bore hole in swine test subject, which was sealed with bone grease and covered with dressing to limit light leakage. The probe depth was adjusted to maximize photoplethysmogram signal, after which the swine was subjected to repeated norepinephrine infusions and a period of controlled hemorrhage followed by fluid resuscitation. Three full swine experiments were completed measuring output from both a piezoelectric (PVD)F sensor and from an optical (PPG) sensor within the same probe, such as the configuration of probe 106. Data was collected successfully over the entire experiment duration (about 4 hours) from both sensors, measuring on three swine.

We used reference instrumentation during swine experiments, which included measurements of blood flow from a laser Doppler flowmeter inserted several centimeters from the modified sensor location, and from trans-cranial Doppler measurements. Laser Doppler flow measurements were unavailable from one swine due to failure of the reference sensor. An unmodified catheter was used to recorder intracranial pressure (ICP), while mean arterial pressure was recorded from an arterial line.

Probe data was analyzed, as follows. Sensor data was analyzed with respect to both broad signal trends and beat-to-beat waveform behavior collected from the PVDF sensor. For blood flow estimation, a metric was first proposed for quantifying the differences between baseline and experimental behavior in order to predict Cerebral vascular resistance (CVR), adapted from prior work on comparative PVDF to PPG signal behavior in peripheral arteries collected using the probe. For each available swine subject, during each cardiac cycle, the computing device (e.g., the signal processor 902) generated an ellipse to fit a hysteresis loop between the PPG and piezoelectric (PVDF) sensor outputs. The long chord of the ellipse was used to approximately represent the amplitude of volume change relative to pressure change, which has been previously demonstrated to track changes in mean arterial diameter in peripheral arteries. The estimated CVR metric is obtained by linear regression of invasive CVR measurement and relative amplitude from first 100 cardiac cycle (baseline). The long chord of an ellipse fit from the baseline is also used in the matric.

Figure 12:
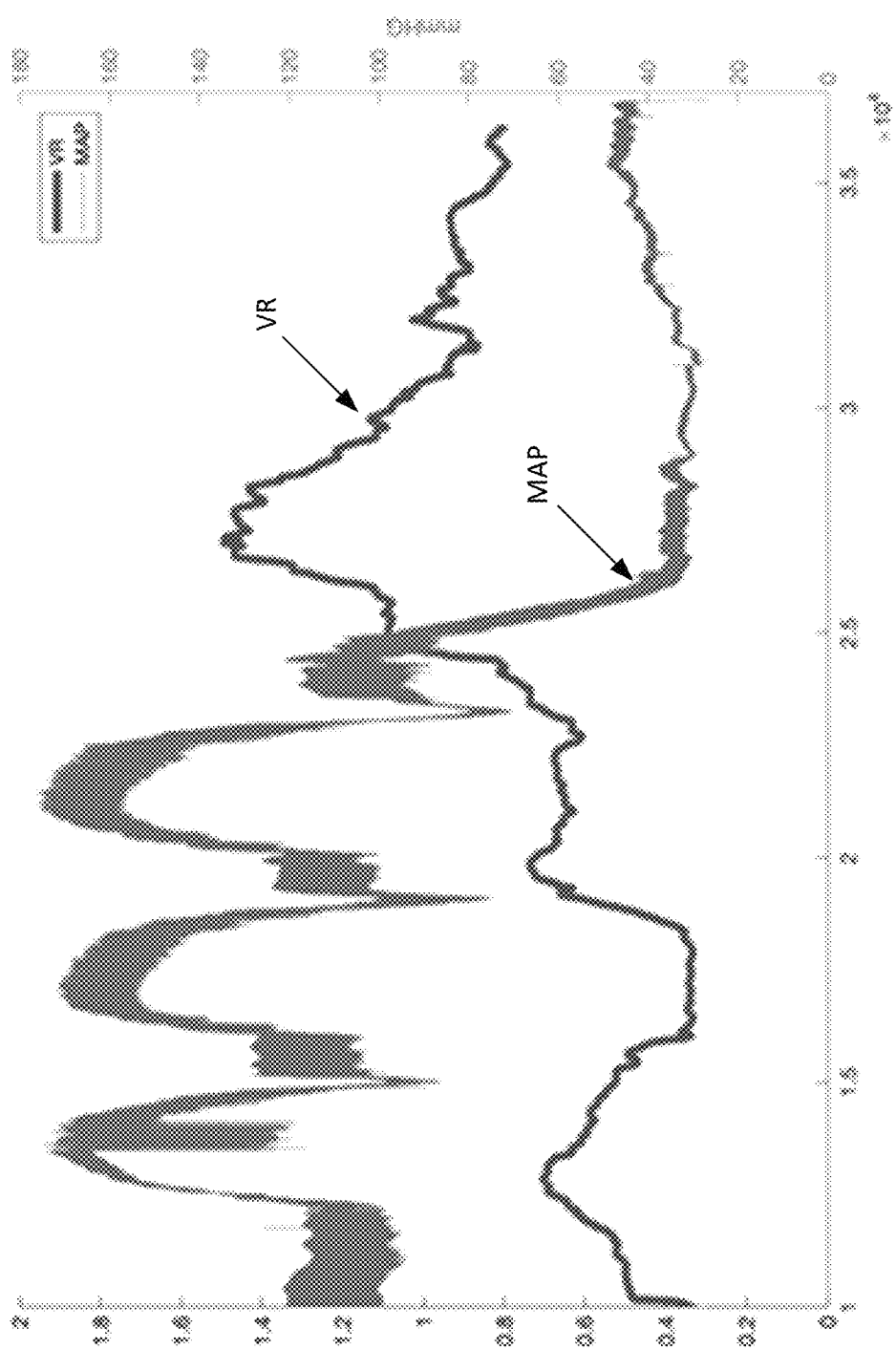
FIG. 12 is a plot of sample trajectories for mean arterial pressure (MAP) and inferred local vascular resistance (VR) from a probe device in accordance with the present techniques for assessing cerebral blood flow for swine undergoing three norepinephrine infusions followed by hemorrhage and resuscitation, in accordance with an example.

The metric for estimated CVR ($\overline{CVR}$) is based on relative amplitude of the ellipse chords, and is formulated:

$$\overline{CVR} = 0.4(L_e - L_b) + 0.2$$

with L being the long chord of an ellipse fit, where subscript e indicates experimental PPG output ratio to the current PVDF output and subscript b indicates the baseline output. A sample trajectory for inferred vascular resistance vs mean arterial pressure (mm HG) for swine 1 is shown in FIG. 12. The x-axis shows time in number of samples at the data logger (e.g., 200 samples per second).

The computing device calculated blood flow from Cerebral perfusion pressure (CPP) and Cerebral vascular resistance (CVR), using:

$$\hat{f} = \frac{CPP}{CVR} = \frac{ABP - ICP}{CVR}$$

where ABP is arterial blood pressure, with both ABP and ICP measured invasively for this data.

In addition, PVDF waveform profiles were extracted between each heartbeat using electrocardiogram (ECG) data to identify beat timing. To obtain representative waveform profiles at various points during the experiments, the computing device averaged ten adjacent cardiac cycles and extracted measurement of peak and valley amplitudes and timing, for both raw and integrated PVDF voltage.

Figure 13A:
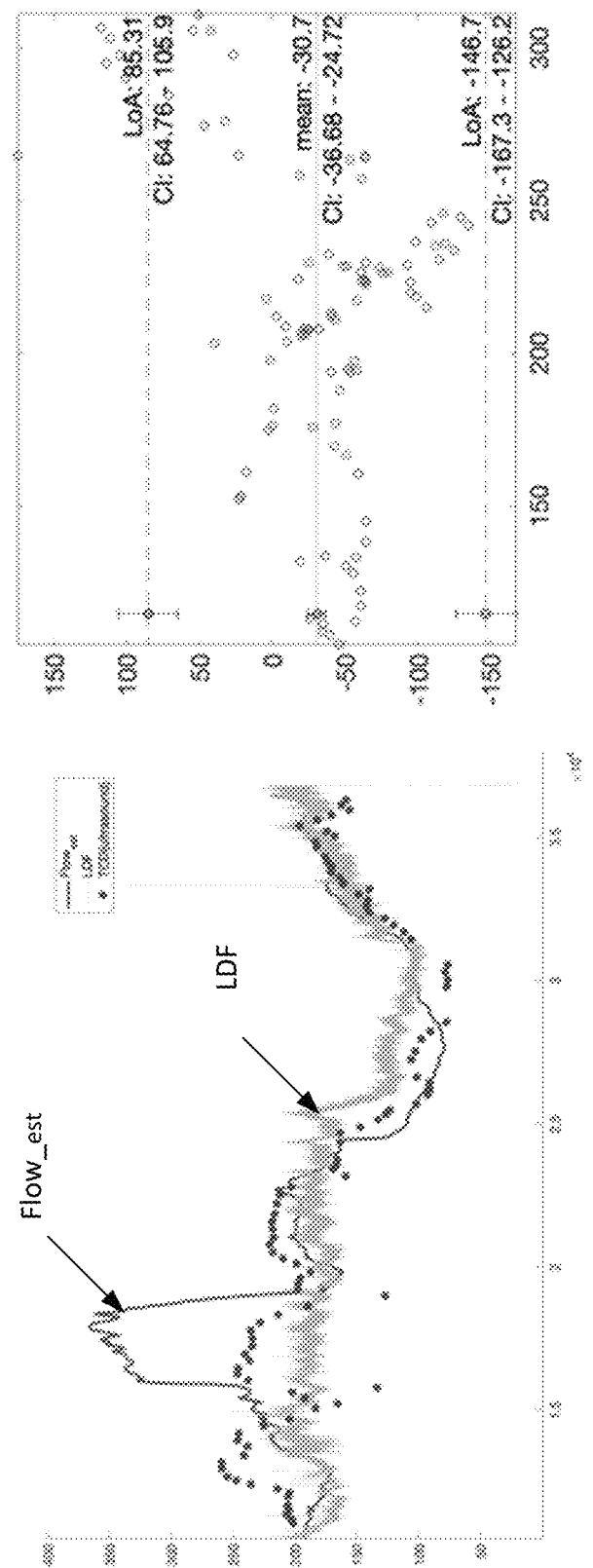
FIGS. 13A-13C illustrate plots of cerebral blood flow estimated from a probe device in accordance with the teachings herein and compared to that obtained using a laser Doppler flowmeter and/or trans-cranial Doppler ultrasound, with the right side of each showing Bland-Altman plots for trans-cranial Doppler vs. PVDF/PPG flow measurements, in accordance with an example.
Figure 13B:
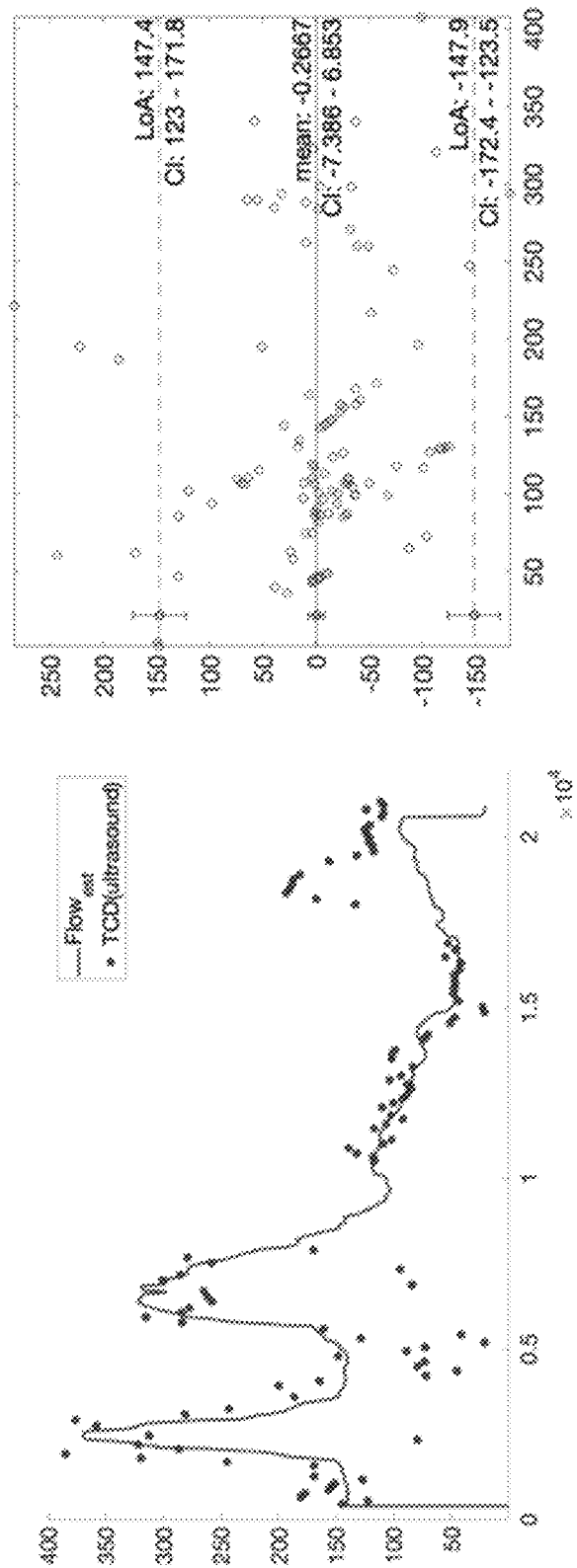
Figure 13C:
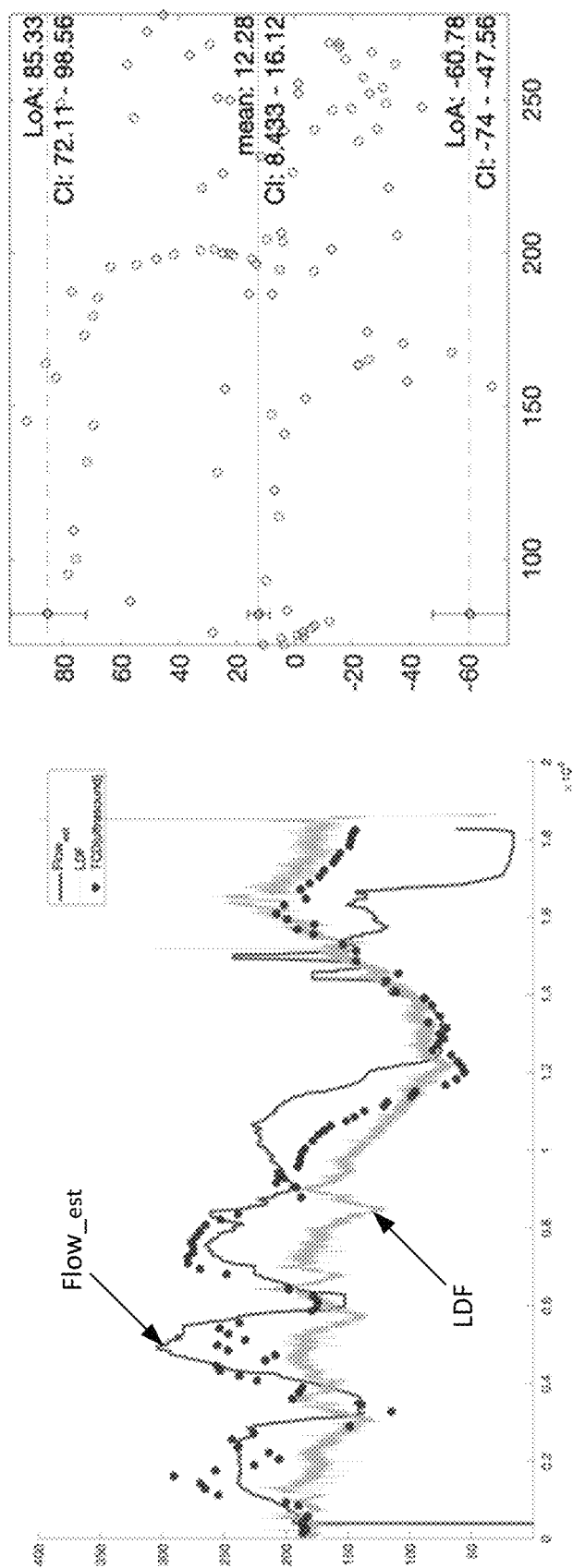

FIGS. 13A-13C show estimated cerebral blood flow using our probe compared to trans-cranial Doppler and laser Doppler flowmeter (when available) measurements. Each of FIGS. 13A-13C show different test results for different swine (with the x-axis showing time in number of samples and the y-axis showing blood pressure units, BPUs, which is a relative unit related to mL/min). Flow amplitude estimated from our probe was in arbitrary units, so it is scaled to the initial flow measured invasively in the plots. In general, changes in the local flow closely track changes measured by reference sensors. In particular, there is close agreement between our sensor and the trans-cranial Doppler measurements in swine 2 (FIG. 13B) and 3 (FIG. 13C), and all three measurement techniques track closely during hemorrhage. Bland-Altman plots for flow estimation with our sensor compared to trans-cranial Doppler are shown on the right side of the FIGS. 13A-13B.

There are also regions where flow estimated by the three methods disagree. For example, during the first half of Swine 1 data collection, as three norepinephrine infusions are applied, our probe first tracks the laser Doppler flowmeter, then tracks neither reference sensor, then reaches agreement with both reference sensors over the three infusions. In swine 2 and 3, during resuscitation, a significant increase in flow is observed as baseline pressure is approached that is not observed in full with our proposed sensor.

We find that beat-to-beat pressure profile measured by the proposed sensor roughly tracks that measured by the conventional ICP monitor, with a delay of approximately 200 milliseconds, in this example. That increase in pressure following each heartbeat is more attenuated, in both signals, than that commonly observed in the periphery. We had hypothesized that the PVDF sensor would capture more signal variation due to hemodynamic phenomena than a conventional ICP sensor. This appears to be the case, especially visible in the raw PVDF sensor output, featuring multiple reflection waves that evolve over time and conditions. However, regardless they show an increased sensitivity our probe provides over conventional systems and the ability to detect cerebral blood differences that conventional techniques cannot. From this experiment, we find that a intracranial catheter in accordance with the techniques herein provides high-quality tracking of blood flow variation when compared to reference flow monitors.

Thus provided herein is a multi-sensor pressure monitoring probe device and system that may be used for applications such as intracranial pressure monitor. In some examples, the probe device is an insertable catheter with a diameter on the order of 50-200 μm, compared to a nominal catheter diameter of 1.35 mm for common other applications. The probe device may contain small diameter optical figures attached to or embedded in a catheter lining to measure blood volume using light reflectivity measurements at one or more wavelengths. The probe device may further include a piezoelectric polymer film attached around the circumference of the catheter to record real-time, beat-to-beat fluctuations in local pressure. An electrical and optical readout circuit connects to wires connected to the piezoelectric film and the terminations of the fiber optic cables. From these detected signals, vascular resistance and local pressure may be estimated. Additional features may include fiberoptic delivery of spectroscopic technologies, allowing for the monitoring of oxygenation and metabolites. For example, the probe designs herein may be further modified to include optodes for fiberoptic delivery of spectroscopic technologies, such as Raman spectroscopy and near infrared spectroscopy that allow monitoring to brain tissue oxygenation and metabolites as well as potentially deliver light at various wavelengths for therapy to the injured brain. In addition, electrical components could be embedded allowing for intra-brain impedance monitoring of brain blood volume, EEG monitoring and even delivering of electrical current such as direct or alternating current as therapy.

The present techniques may be further implemented using a multi-sensor catheter device with an optical sensors that measure tissue oxygenation and mitochondrial function using near infrared and/or near ultraviolet wavelengths and differential absorption spectroscopy or resonance Raman spectroscopy. By measuring reflected light or scattered Raman light, changes in absorption amounts can be detected and correlated to changes in oxygenation levels in the brain. Such brain tissue oxygenation ($PtO_2$) can be used to complete techniques such as ICP. This optical data can be fed into an estimate, along with pressure data from the catheter, to identify waveform matches between brain metabolism and vascular function.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A pressure sensing system comprising:
   an insertable catheter having a distal end and a proximal end;
      a pressure sensor at the distal end of the insertable catheter and configured to measure first pressure data of a sample region within a subject;
      an optical sensor positioned proximally from the pressure sensor and configured to illuminate an optical sample region and to collect reflected illumination from the optical sample region, the reflected illumination corresponding to blood volume in the optical sample region;
      a piezoelectric pressure sensor positioned adjacent the optical sensor and covering a periphery of the insertable catheter, the piezoelectric pressure sensor configured to measure pressure data for the optical sample region; and
   a processing device configured to
      receive the reflected illumination from the optical sensor,
      receive the pressure data from the piezoelectric pressure sensor, and
      analyze the pressure data from the piezoelectric pressure sensor and the reflected illumination, heartbeat-by-heartbeat, and determine (i) vascular resistance over the optical sample region, (ii) a blood flow over the optical sample region, and (iii) pressure over the optical sample region.

2. The pressure sensing system of claim 1, wherein the optical sensor comprises an illumination optical fiber and a collection optical fiber.

3. The pressure sensing system of claim 2, wherein the illumination optical fiber and the collection optical fiber are each positioned within respective opposing grooves of the insertable catheter.

4. The pressure sensing system of claim 1, wherein the piezoelectric pressure sensor comprises at least one piezoelectric layer and at least one encapsulating layer covering the piezoelectric layer.

5. The pressure sensing system of claim 4, wherein the piezoelectric pressure sensor comprises at least one other encapsulating layer covering the piezoelectric layer.

6. The pressure sensing system of claim 5, wherein the piezoelectric pressure sensor is positioned to cover the entire periphery of the insertable catheter coinciding with the optical sample region.

7. The pressure sensing system of claim 1, wherein the insertable catheter has an outer most diameter of less than 2 mm.

8. The pressure sensing system of claim 7, wherein the outer most diameter is less than or equal to 1.5 mm.

9. The pressure sensing system of claim 7, wherein the outer most diameter is from 0.8 mm to 1.0 mm.

10. The pressure sensing system of claim 1, wherein the pressure sensor at the distal end of the insertable catheter is an intracranial pressure sensor and the insertable catheter is an intracranial pressuring sensor catheter.

11. The pressure sensing system of claim 1, further comprising a photodetector assembly communicatively coupled to the processing device.

12. The pressure sensing system of claim 1, wherein the processing device comprises a readout circuit.

13. The pressure sensing system of claim 1, wherein the processing device is configured to determine vascular resistance of the region over the optical sample region from the pressure data from the piezoelectric pressure sensor and the reflected illumination.

14. The pressure sensing system of claim 13, wherein the processing device is configured to determine the blood flow over the optical sample region from the vascular resistance and the first pressure data from the pressure sensor at the distal end of the insertable catheter.

15. The pressure sensing system of claim 14, wherein the processing device is configured to determine the blood flow over the optical sample region from the vascular resistance, the first pressure data from the pressure sensor at the distal end of the insertable catheter, and a mean arterial pressure data.

16. The pressure sensing system of claim 14, wherein the processing device is further configured to analyze the blood flow over a sampling time period and to determine changes in pressure over the sampling time period, wherein the changes in pressure of the sampling time period indicate autoregulation in the sample region.

17. The pressure sensing system of claim 1, wherein the insertable catheter further comprises a temperature sensor, an actigraphy sensor, or an impedance sensor.

18. A pressure sensing system comprising:
an insertable catheter having a distal end and a proximal end;
a pressure sensor at the distal end of the insertable catheter and configured to measure first pressure data of a sample region within a subject;
an optical sensor positioned proximally from the pressure sensor and configured to illuminate an optical sample region and to collect reflected illumination from the optical sample region and to determine a differential absorption spectroscopy or to collect scattered illumination from the optical sample region and determine a resonance Raman spectroscopy, the reflected illumination or scattered illumination corresponding to tissue oxygenation and/or mitochondrial function in the optical sample region;
a piezoelectric pressure sensor positioned adjacent the optical sensor and covering a periphery of the insertable catheter, the piezoelectric pressure sensor configured to measure pressure data for the optical sample region; and
a processing device configured to
receive the reflected illumination data or scattered illumination data from the optical sensor,
receive the pressure data from the piezoelectric pressure sensor, and
analyze the pressure data from the piezoelectric pressure sensor and the reflected illumination data or scattered illumination data, heartbeat-by-heartbeat, and determine (i) tissue oxygenation and mitochondrial function over the optical sample region, (ii) a blood flow over the optical sample region, and/or (iii) pressure over the optical sample region.

* * * * *

UNITED STATES PATENT AND TRADEMARK OFFICE
CERTIFICATE OF CORRECTION

| | |
|---|---|
| PATENT NO. | : 11,779,235 B2 |
| APPLICATION NO. | : 16/793650 |
| DATED | : October 10, 2023 |
| INVENTOR(S) | : Ward et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 562 days.

Signed and Sealed this
Twelfth Day of November, 2024

Katherine Kelly Vidal
*Director of the United States Patent and Trademark Office*